(12) United States Patent
Cerioli

(10) Patent No.: US 8,585,626 B2
(45) Date of Patent: Nov. 19, 2013

(54) BRACE FOR DYNAMICALLY CORRECTING THE BENDING OF THE JOINTS OF THE LOWER LIMB

(76) Inventor: Mario Cerioli, Castelleone (IT)

( * ) Notice: Subject to any disclaimer, the term of this patent is extended or adjusted under 35 U.S.C. 154(b) by 295 days.

(21) Appl. No.: 13/063,269

(22) PCT Filed: Oct. 7, 2009

(86) PCT No.: PCT/IB2009/007070
§ 371 (c)(1),
(2), (4) Date: Mar. 10, 2011

(87) PCT Pub. No.: WO2010/041128
PCT Pub. Date: Apr. 15, 2010

(65) Prior Publication Data
US 2011/0160630 A1   Jun. 30, 2011

(30) Foreign Application Priority Data

Oct. 9, 2008 (IT) ............................. CR2008A0021

(51) Int. Cl.
*A61F 5/00* (2006.01)
(52) U.S. Cl.
USPC ......................................................... 602/23
(58) Field of Classification Search
USPC ............ 602/23, 26, 27, 24, 25; 128/869, 882; 623/39, 46, 31–32; 482/121, 124, 127, 482/128
See application file for complete search history.

(56) References Cited

U.S. PATENT DOCUMENTS

| | | | | | |
|---|---|---|---|---|---|
| 932,177 | A | * | 8/1909 | Roth | 602/23 |
| 3,230,952 | A | * | 1/1966 | Reyes | 602/16 |
| 4,252,112 | A | * | 2/1981 | Joyce | 602/26 |
| 4,387,709 | A | * | 6/1983 | Shen | 602/26 |
| 4,408,600 | A | * | 10/1983 | Davis | 602/16 |
| 4,422,453 | A | * | 12/1983 | Salort | 602/23 |
| 4,456,003 | A | * | 6/1984 | Allard et al. | 602/16 |
| 5,330,417 | A | * | 7/1994 | Petersen et al. | 602/16 |
| 6,004,282 | A | * | 12/1999 | Whitley | 602/5 |
| 6,428,495 | B1 | * | 8/2002 | Lynott | 602/23 |
| 6,790,193 | B2 | | 9/2004 | Wellershaus et al. | |

FOREIGN PATENT DOCUMENTS

| | | |
|---|---|---|
| DE | 200 05 366 U1 | 7/2001 |
| EP | 1 138 287 A1 | 10/2001 |
| FR | 1 552 131 A | 1/1969 |

OTHER PUBLICATIONS

International Search Report, dated Apr. 16, 2010, from corresponding PCT application.

* cited by examiner

*Primary Examiner* — Patricia Bianco
*Assistant Examiner* — Raymond E Harris
(74) *Attorney, Agent, or Firm* — Young & Thompson

(57) ABSTRACT

A brace for dynamically correcting the bending of the joints of the lower limb including a thigh grip (1), a leg grip (2), connection means between said thigh grip and said leg grip, wherein said connection means includes at least two flat flexible profiles (3', 3") that work in extension, elastically opposing the bending of the knee, and said brace comprises a foot grip (7) and further flexible means (6, 3'a, 3"a) arranged for connecting said leg grip (2) to said foot grip (7), which work in extension elastically opposing the bending of the ankle.

10 Claims, 2 Drawing Sheets

BRACE FOR DYNAMICALLY CORRECTING THE BENDING OF THE JOINTS OF THE LOWER LIMB

BACKGROUND OF THE INVENTION

The invention relates to a mechanical brace and in particular to an ankle, knee and hip orthesis, aimed at preventing and correcting deformation in bending of the joints, and at developing dynamic balance in children with motor development disorder.

In subjects affected by cerebral pathologies of prenatal or perinatal origin, the tendency to adopt a bent position of the knee joint often develops, due to insecurity that derives from adoption of an aligned erect position. This unnatural position tends to cause progressive lengthening of the extensor tendons, with shortening of the flexors, which over time causes a worsening of the condition of the subject, also with involvement of the other joints of the lower limb, i.e. the ankle and hip joints.

To attempt to prevent or correct deformation in the bending of the knee in the child or adult, devices are used, which are fitted to the limbs to correct the defect in posture and carriage.

For example, is known the use of plaster or plastic casts, from thigh to foot or from thigh to leg, which immobilize the joint for a certain period of time.

The use of thigh-leg braces is also known, wherein connection between the thigh grip and the leg grip consists of a rigid metal splint and the knee joint is made to extend by elastic compression exerted on the patella.

The use of thigh-leg braces is also known, wherein the connection between thigh cuff and leg cuff is produced by means of rigid splints connected by a mechanical joint, substantially obtained with a hinged joint, coaxial with the anatomical knee joint.

Another known solution is the use of a canvas casts, from thigh to leg, secured to the limb with straps and Velcro® fixings, which comprise metal or plastic splints inserted in fabric pockets that extend, parallel to each other, along the entire length of the cast.

The patent DE 200 05 366 U1 discloses a brace for dynamically correcting the bending of the knee comprising a thigh grip, a leg grip and connection means between said thigh grip and said leg grip, where said connection means comprise two flat flexible profiles that work in extension, elastically opposing the bending of the knee. However, this embodiment does not allow correction of the bending of the ankle and hip joints, which must be usually implemented in children with motor development disorder. Moreover, it does not allow freedom of movement and changes of position that are typical needs of the child, and therefore becomes intolerable to the wearer.

The defects of currently known devices consist essentially in that fact that:
- they are heavy and cumbersome devices;
- they limit the freedom of the person, reducing the possibility of movement;
- they limit the functional exercise of walking, with anti-therapeutic effect;
- they hamper passage from a sitting or lying position to an upright posture;
- they cause excessive heating of the limb during the summer season;
- they are generally not well tolerated, particularly by children.

SUMMARY OF THE INVENTION

The aim of the present invention is to overcome the aforesaid defects. This aim is achieved by means of a brace for dynamically correcting the bending of the joints of the lower limb comprising:
- a thigh grip;
- a leg grip;
- connection means between said thigh and leg grip, wherein said connection means comprise at least two flat flexible profiles that work in extension, elastically opposing the bending of the knee, characterized in that said brace comprises a foot grip and further flexible means arranged for connecting said leg grip to said foot grip, which work in extension elastically opposing the bending of the ankle. Advantageously, said flat flexible profiles are in the form of an elongated "S".

According to an aspect of the invention, the thigh grip comprises a band of inextensible material, advantageously polypropylene, provided with reversible closing means arranged on the side of the thigh.

According to a further aspect of the invention, the leg grip comprises a band of inextensible material, advantageously polypropylene, provided with reversible closing means arranged on the front portion of the leg.

Advantageously, said band forming the leg grip extends posteriorly to the leg with a shaped element made of flexible plastic material arranged for lying along the calf and the heel of the wearer of the brace, fixing to a foot grip that encircles the sole of the foot of the wearer.

In a preferred embodiment of the invention, two profiles are arranged symmetrically with respect to a sagittal plane normal to the axis of rotation of the knee joint, wherein the upper ends are fixed to the anterior portion of the thigh grip, while the lower ends of said profiles are laterally fixed to the leg grip.

According to a variant, said fixing means of the profiles to the thigh and leg grip are of reversible type, so as to allow replacement of said profiles.

According to a preferred embodiment of the invention, said flat flexible profiles continue beyond said leg grip, connecting the leg grip to said foot grip.

According to a further preferred embodiment of the invention, the dynamic brace also comprises a pelvis grip and at least one of said flat flexible profiles further connects said thigh grip to the pelvis grip. According to other embodiments, the flat flexible profiles can comprise a bundle of profiles or threadlike elements, with the same or different flexibility, and the fixing means to the thigh and leg grips are arranged for allowing a sliding of the profiles to adjust the length of the portions positioned above or below them.

The advantages achieved with the present invention essentially consist in the fact that the brace:
- is light and well tolerated;
- is easy to wear and adjustable to the physical structure and to the functional characteristics of the wearer;
- does not immobilize the knee, ankle and hip joint and instead it allows to be used during the functional exercise of spontaneous walking of the wearer, above all the child, in his social contexts;
- does not hamper the passage from the sitting or lying position to the upright posture;
- it allows effective dynamic correction of the bending of the knee to be achieved over time;

it allows treatment of motor development disorder in relation to the entire muscle chain of one or more limbs.

BRIEF DESCRIPTION OF THE DRAWINGS

The advantages of the invention will be more apparent in the following description of preferred embodiments, by way of a non-limiting example, and with the aid of the figures wherein.

DESCRIPTION OF PREFERRED EMBODIMENTS

Figure 1:
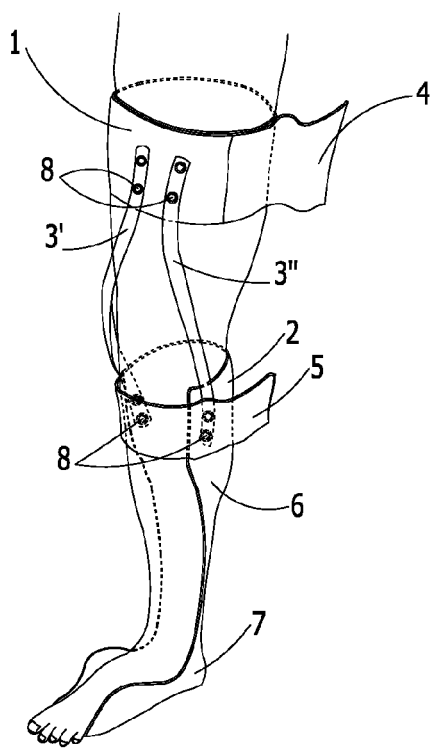
FIGS. 1 and 2 represent, in axonometric view, a brace for dynamically correcting the bending of the joints of the lower limb applied to a left leg respectively in an erect and bent position according to a first embodiment of the invention.
Figure 2:
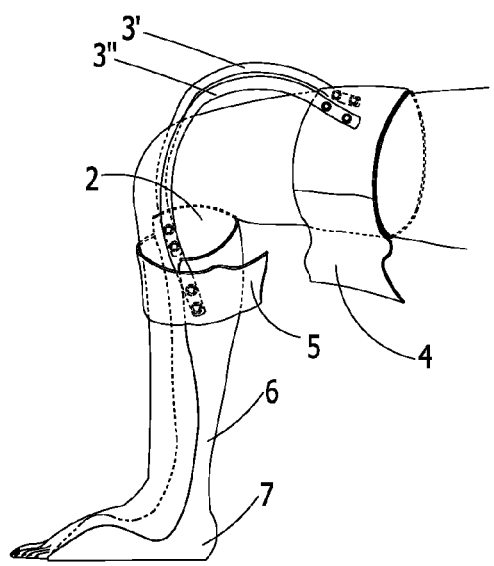
Figure 3:
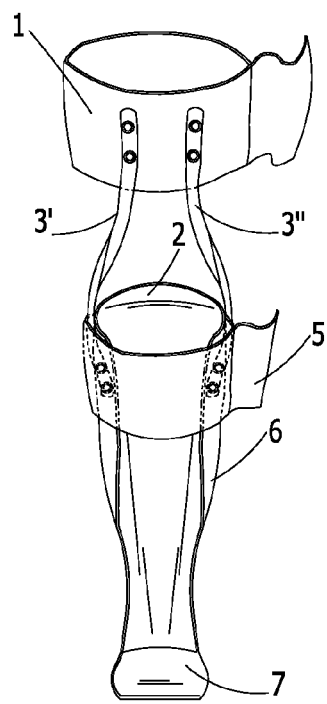
FIGS. 3 and 4 represent, in a front and side axonometric view, the brace of FIGS. 1 and 2.
Figure 4:
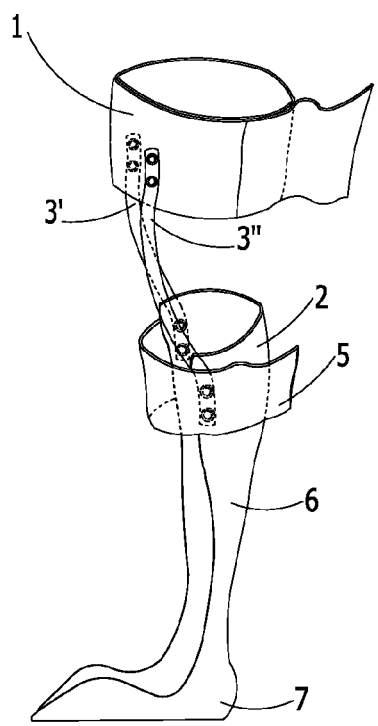

With reference to the figures, the brace comprises a thigh grip 1, a leg grip 2 and two flat flexible profiles 3' and 3" that connect, in a non-rigid elastic manner, the thigh grip 1 to the leg grip 2.

The thigh grip 1 comprises a band of inextensible material, such as polypropylene or other plastic, metal or composite material of known type, open on the side of the thigh, where reversible closing means are present, for example formed by a band 4 fixable to the thigh grip by Velcro®.

The leg grip 2 comprises a band of inextensible material analogous to that of the thigh grip, open in the anterior portion of the leg, where reversible closing means are present, analogous to those of the thigh grip, comprising a band 5.

With particular reference to FIGS. 1-4, the band forming the leg grip 2 extends posteriorly to the leg itself with a shaped element 6 made of flexible plastic material arranged for lying along the calf and a substantially rigid shaped element 7 arranged for containing the heel and forefoot of the wearer of the brace, acting as foot grip.

The two flat flexible profiles 3' and 3" are made of material arranged for acting as a flat spring and are shaped in the form of an S elongated towards the top, so as not to interfere with the patella during movement of the wearer of the brace.

They are arranged symmetrically with respect to a sagittal plane normal to the axis of rotation of the knee joint, and the upper ends are fixed to the anterior portion of the thigh grip, while the lower ends of said profiles are fixed to the leg grip laterally to the leg itself.

The fixing means of the ends of the flat flexible profiles 3' and 3" to the thigh and leg grips are alternatively produced with rivets 8 or with screws or other means of known type, so that the profiles can be replaced over time, to follow the physiological development and functional progress of the wearer of the brace.

Figure 5:
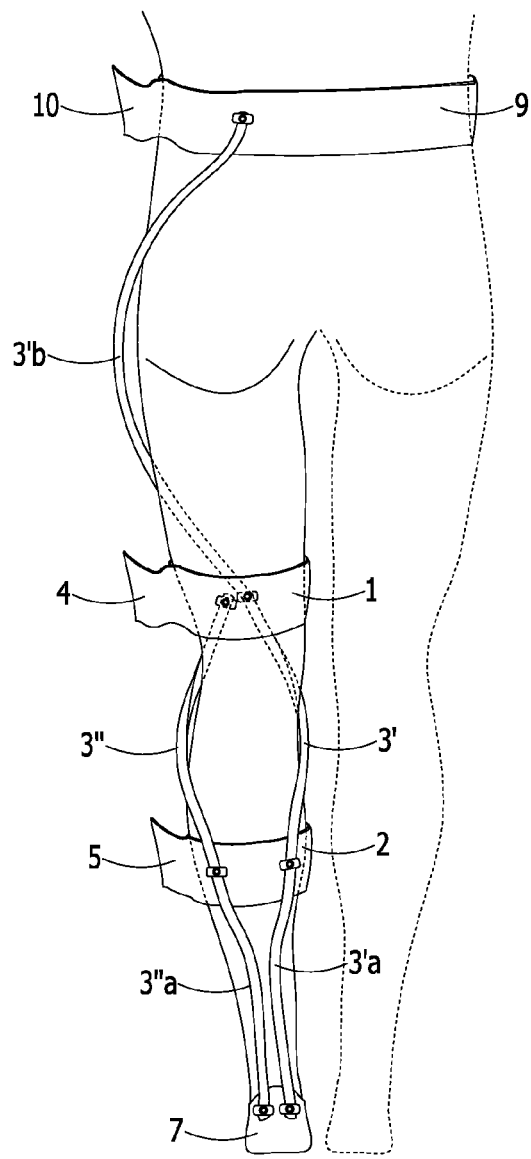
FIGS. 5 and 6 represent, in a side and rear view, a brace for dynamically correcting the bending of the joints of the lower limb applied to a left leg according to a further embodiment of the invention.
Figure 6:
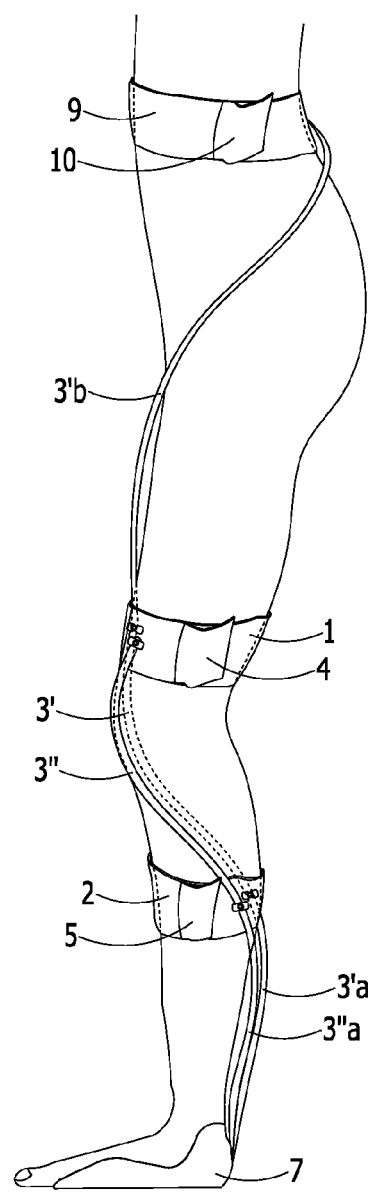

With reference to FIGS. 5 and 6, these show a variant of embodiment of the dynamic brace comprising a pelvis grip 9.

The pelvis grip 9 comprises a band of inextensible material, such as polypropylene or other plastic or metal or composite material of known type, provided with reversible closing means, for example formed of a band 10 fixable to the pelvis grip by Velcro®.

The flat flexible profiles 3' and 3" continue downward beyond the leg grip 2, through extensions 3'*a* and 3"*a* that elastically connect this grip to the foot grip 7.

At least one of said profiles further extends upward beyond the thigh grip 1, and in particular it is the profile 3' that, by means of an extension 3'*b*, elastically connects the thigh grip 1 to the pelvis grip 9. The fixing means of the ends of the flat flexible profiles 3', 3", 3'*a*, 3"*a* and 3'*b* to the thigh, leg, foot and pelvis grips are alternatively produced with rivets or screws or other reversible means of known type, so that the profiles can be replaced over time, to follow the physiological development and functional progress of the wearer of the brace.

The fixing means of the flat flexible profiles 3' and 3" and of their extensions can also be provided internally with sliding guides for these profiles, to allow reversible fixing and variation of the length of the portions of profile positioned above and below them.

The flat flexible profiles 3' and 3" can be continuous or made by discontinuous portions, fixed between the pelvis, thigh, leg and foot grips.

Finally, the flat flexible profiles 3' and 3" can comprise a bundle of profiles or threadlike elements, with the same or different flexibility according to the needs of the wearer of the brace and of the progress made.

In use, the subject undergoing rehabilitation wears the brace thanks to the reversible closing means positioned on the thigh and leg grip and, if necessary, on the pelvis and foot grip.

During movements of the patient the flat flexible profiles behave like flat springs that are loaded during bending of the knee and of the other joints of the lower limbs and that return elastic energy during extension of the knee and of the other joints involved, promoting in this manner adoption of an upright and aligned posture.

During the rehabilitation therapy the physician may decide to replace the flat flexible profiles choosing to use profiles with flexibility suitable for the progress of the patient, provided with the brace in a kit comprising profiles of different flexibility.

Of course, those skilled in the art may choose different materials suitable for the aim, always achieving the advantages set forth above.

The invention claimed is:

1. A brace for dynamically correcting the bending of joints of a lower limb that has a thigh, a knee, a calf, an ankle, and a foot, the brace comprising:
  a thigh grip (1) having an anterior part, a posterior part, and lateral side parts and that is adapted to be attached to the thigh above the knee;
  a leg grip (2) having an anterior part, a posterior part, and lateral side parts and that is adapted to be attached to the calf below the knee;
  at least two flat flexible springs profiles (3', 3") that work in extension, elastically opposing bending of the knee, said two flat flexible springs having upper end portions attached to the anterior part of said thigh grip and lower end portions attached to the respective lateral side parts of said leg grip;
  a foot grip (7) having an anterior part and a posterior part; and
  a shaped element (6) for connecting said leg grip (2) to said foot grip (7), said shaped element (6) extending along a posterior of the calf and having an upper end portion attached to the lateral side parts of the leg grip and a lower end portion attached to the posterior part of said foot grip.

2. The brace according to claim 1, wherein said flat flexible springs (3', 3") are arranged symmetrically with respect to a sagittal plane normal to the axis of rotation of the knee.

3. The brace according to claim 2, wherein said flat flexible springs (3', 3") are shaped in the form of an elongated "S".

4. The brace according to claim 1, wherein said thigh grip (1) comprises a band of inextensible material provided with reversible closing means (4) arranged on one of the lateral side parts.

5. The brace according to claim 1, wherein said leg grip (2) comprises a band of inextensible material provided with reversible closing means (5) opening at the anterior part.

6. The brace according to claim 1, wherein said further flexible means comprise a shaped element (6) made of a flexible plastic material that conforms to and lies along a posterior of the calf continuously from the leg grip to the foot grip.

7. The brace according to claim 1, further comprising reversible fixing means for fixing said at least two flat flexible springs to the respective leg and thigh grips and for allowing replacement of the at least two flat flexible springs.

8. The brace according to claim 1, wherein said flat flexible springs (3', 3") are provided in a kit comprising plural said flat flexible springs of different flexibility.

9. A brace for dynamically correcting the bending of joints of a lower limb that has a thigh, a knee, a calf, an ankle, and a foot, the brace comprising:

a thigh grip (1) having an anterior part, a posterior part, and lateral side parts and that is adapted to be attached to the thigh above the knee;

a leg grip (2) having an anterior part, a posterior part, and lateral side parts and that is adapted to be attached to the calf below the knee;

at least two flat flexible springs profiles (3', 3") that work in extension, elastically opposing bending of the knee, said two flat flexible springs having upper end portions attached to the anterior part of said thigh grip and lower end portions attached to the respective lateral side parts of said leg grip;

a foot grip (7) having an anterior part and a posterior part; and further flexible means for connecting said leg grip (2) to said foot grip (7), which work in extension elastically opposing bending of the ankle said further flexible means extending along a posterior of the calf and having an upper end portion attached to the lateral side parts of the leg grip and a lower end portion attached to the posterior part of said foot grip, wherein said further flexible means comprises extensions (3'*a*, 3"*a*) of said flat flexible springs (3', 3") that continue downward beyond the leg grip (2) to the foot grip (7), wherein said extensions are attached to the lateral side parts of said leg grip and the posterior part of said foot grip.

10. The brace according to claim 9, further comprising a pelvis grip (9) and wherein one of said two flat flexible springs comprises an extension (3'*b*) that extends upward from the anterior part of the thigh grip (1), elastically connecting the thigh grip to a posterior part of the pelvis grip (9).

\* \* \* \* \*